United States Patent [19]

Sinkoff et al.

[11] 4,402,986

[45] Sep. 6, 1983

[54] BULK STARTER MEDIA

[75] Inventors: Brian A. Sinkoff, Oak Park; Robert H. Bundus, Rochester, both of Mich.

[73] Assignee: Stauffer Chemical Company, Westport, Conn.

[21] Appl. No.: 286,088

[22] Filed: Jul. 23, 1981

[51] Int. Cl.$^3$ .................. A23C 21/02; A23C 9/12; C12N 1/20

[52] U.S. Cl. .................... 426/41; 426/36; 426/43; 426/583; 435/253

[58] Field of Search .......... 426/34, 583, 41, 42, 426/43, 36, 61; 435/253

[56] References Cited

U.S. PATENT DOCUMENTS

| | | | |
|---|---|---|---|
| 290,253 | 12/1883 | Marsh | 435/139 |
| 1,849,053 | 3/1932 | Bernhauer et al. | 435/137 |
| 1,913,346 | 6/1933 | Stiles | 435/42 |
| 2,032,443 | 3/1936 | Schultz et al. | 435/139 |
| 2,422,230 | 6/1947 | Foster et al. | 435/84 |
| 2,424,832 | 7/1947 | Koerber | 435/43 |
| 2,448,790 | 9/1948 | Foster et al. | 435/43 |
| 2,549,765 | 4/1951 | Beesch et al. | 435/140 |
| 2,609,329 | 9/1952 | Niedercorn | 435/64 |
| 3,354,049 | 11/1967 | Christensen | 435/253 |
| 3,429,777 | 2/1969 | Bode | 435/139 |
| 3,677,897 | 7/1972 | Jeffreys | 435/253 |
| 3,714,063 | 1/1973 | Salomone | 252/312 |
| 3,728,279 | 4/1973 | Salomone | 435/253 X |
| 3,852,158 | 12/1974 | Anderson et al. | 426/43 X |
| 3,961,078 | 6/1976 | Stitt | 426/41 |
| 3,998,700 | 12/1976 | Reinbold et al. | 426/43 X |
| 4,020,185 | 4/1977 | Anderson et al. | 426/36 |
| 4,053,642 | 10/1977 | Hup et al. | 426/36 |
| 4,053,643 | 10/1977 | Corbin, Jr. | 426/40 |
| 4,115,199 | 9/1978 | Porubcan et al. | 426/43 X |
| 4,259,357 | 3/1981 | Van Kranenburg | 426/42 |
| 4,275,154 | 6/1981 | Hall | 435/32 |
| 4,282,255 | 8/1981 | Sandine et al. | 426/36 X |

FOREIGN PATENT DOCUMENTS 1024393 1/1978 Canada .

OTHER PUBLICATIONS

Waksman, Microbial Antagonism and Antibiotic Substances, Second Edition, (1947), The Commonwealth Fund, pp. 64 and 65.

*Primary Examiner*—David M. Naff
*Attorney, Agent, or Firm*—Paul J. Juettner

[57] ABSTRACT

Bulk starter media for making cheese is prepared having internal pH control by providing in conventional starter media an amount of magnesium ammonium phosphate sufficient to maintain a pH of at least 5 for at least 20 hours during fermentation to produce a cultured bulk starter. The magnesium ammonium phosphate is less than 50% soluble at a pH of from 6 to about 7.5 of the starter media prior to fermentation. The starter media preferably contains an alkali metal tripolyphospate phage control agent, and may contain sweet whey and autolyzed yeast.

33 Claims, No Drawings

BULK STARTER MEDIA

BACKGROUND OF THE PRESENT INVENTION

1. Field of the Invention

The present invention relates to bulk starter media for cheese making characterized by improved buffering and bacteriophage inhibition without affecting physical stability.

2. Description of the Prior Art

In the commerical production of cheese, large vats of milk are treated with a milk clotting agent such as rennin and inoculated with acid producing bacteria and optionally flavor producing organisms to provide the desired acid conditions for cheese making as well as the desired flavor, body, odor and texture characteristics of the resulting cheese.

The term "acid producing bacteria" refers to bacteria capable of fermenting lactose or other similar carbohydrates to produce, mainly, lactic acid, such as *Streptococcus lactis*, *Streptococcus cremoris*, *Lactobacillus bulgaricus*, and *Streptococcus thermophilus*.

The term "flavor-producing bacteria" refers to bacteria capable of fermenting citric acid or citrates at a favorable pH with the production of flavor producing compositions illustrated by diacetyl, acetylmethylcarbinol, and volatile material such as carbon dioxide, such as *Leuconostoc citrovorum* (*Streptococcus citrovorus*) and *Leuconostoc dextranicum* (*Streptococcus paracitrovorus*) and subspecies thereof. *Streptococcus diacetylactis* produces both lactic acid and flavor constituents.

The bacteria or culture is generally propagated from a mother culture in large enough quantities of milk (about 1% of the final volume) to produce a bulk starter, which can then be used for fermenting the final batch of milk to produce the end product, i.e., cheese.

A good starter must produce lactic acid in the cheese vat at a vigorous and steady rate. "Slow" starters produce cheese of inferior quality. Some of the most significant causes of starter slowness and failure is (1) bacteriophage, hereinafter "phage" (2) bacteria of low viability, and (3) low bacterial cell population.

It has been found that the composition of the starter medium exerts a considerable influence on the loss of cell viability due to phage attack. Media constituents such as milk, amino acids, vitamins and tryptophan, and particularly calcium ions, may be necessary for full bacteriophage activity. If the starter culture is grown in a calcium ion deficient medium, the culture is protected because a phage, if present, will die out (Davis ibid, at page 215).

Various bulk starter media have been formulated to promote bacterial growth and inhibit phage. The ingredients of seven such media are listed in Table I below:

TABLE I

General Composition of Several Bulk Starter Media 1

| Ingredient | A | B | C | D | E | F | G |
|---|---|---|---|---|---|---|---|
| NFDM | + | + | + | + | + | + | − |
| Dextrose | + | + | + | − | + | − | − |
| Ammonium phosphate | + | + | + | − | + | − | − |
| Dextrin | + | + | + | − | + | − | − |
| Sodium phosphate | + | + | + | − | + | − | − |
| Starch | + | − | − | − | + | − | − |
| Demineralized whey | + | − | − | − | − | + | + |
| Pancreas extract powder | + | + | − | − | − | − | − |
| Lactose | − | − | + | + | − | − | − |
| Whey Powder | − | − | + | − | + | − | − |
| Sucrose | − | − | + | − | − | − | − |
| Yeast Extract | − | − | + | + | + | + | + |
| Sodium Citrate | − | − | − | − | + | − | − |
| Hydrolyzed cereal solids 2 | − | − | − | − | − | + | − |
| Phosphate-citrate buffer | − | − | − | + | − | + | + |

1 T. J. Gulstrom et al., J. Dairy Sci. 62:208–221 (1979)
2 Cereal not identified Another bulk starter medium, disclosed in Canadian Pat. No. 1,024,393, can be formulated by blending 4.14 kilograms (9.2 lbs.) of the following mixture with 380 liters (100 gallons) of whey:

| | |
|---|---|
| 36.4% | Sodium dihydrogen phosphate |
| 34.5% | Disodium phosphate |
| 19% | Autolyzed yeast extract |
| 9% | Hydrolyzed casein |
| 0.48% | Magnesium sulfate |
| 0.1% | Ferrous sulfate |
| 0.1% | Manganese sulfate |
| 0.1% | Sodium chloride |
| 99.78% | |

The autolyzed yeast extract and the hydrolyzed casein used in this medium acts as a stimulant for the growth of lactic acid producing bacteria. Dextrose and other sugars and dextrins are useful to accelerate the initial development of the culture and reduce the initial lag phase of the culture in fermenting lactose. Trace minerals such as magnesium (less than 1%) and manganese as well as ferrous sulfate are known in the art to be beneficial to lactic acid culture systems.

For phage control, the media examples above have been formulated without calcium or with calcium binding systems. It is well known that orthophosphate salts are effective in binding the calcium to prevent the calcium from promoting phage growth (Davis ibid, pp. 215, 237 and 238; Canadian Pat. No. 1,024,393; R. E. Hargrove et al, 1961, Journal of Dairy Science 44 pp. 1799-1810). Citrate buffers are also effective in phage control (Gulstrom et al., ibid; Anderson et al., U.S. Pat. No. 3,852,158 as well as Doull and Meanwell, Procedures, 13th International Dairy Congress, 3:114 (1953); and Rountree, Australian J. Experimental Biology and Medical Science 25, p. 203 (1947).

Even though some phage control can be effected with orthophosphates and citrates, the high concentrations of these salts which are required for phage control also suppress the growth of lactic acid producing bacteria as compared to their growth in skim milk and other media of relatively low ionic strength.

Salts that lower the ionic calcium to below 0.1 ppm. to achieve phage control often also cause physical instability of the starter, slow the starter activity or both and may weaken the gel strength of cheese curd.

A commercially useful bulk starter medium preferably should be formulated to preserve the stability of the protein in the medium upon heating. All bulk starter media must be pasteurized prior to inoculation. An improper selection of salts could cause the protein of a medium to form a curd or precipitate upon pasteurization. A heavy protein precipitate in a starter usually results in the undesirable discoloration of the curd in the bottom of the cheese vat.

Further, skim milk and most other starter media have limited acid buffering capacity from protein, salts or both. The speed of acid development when bulk starter is added to the cheese vat is a function of the total number of viable organisms in the starter as well as their position in the growth phase. Since bacterial growth is pH dependent, the number of bacteria which can be achieved in a starter and their position in the growth phase at the time of inoculation into the cheese vat is dependent upon the number of generations that can be produced before the pH of the medium drops to a value that slows, stops or inhibits the log phase of bacterial growth.

Three systems for controlling acid development and pH are: continuous neutralization by the external addition of base (gaseous ammonia or ammonium hydroxide) during culture growth, use of a highly buffered medium and neutralization after growth of the culture (pH Control During Lactic Starter Production, N. F. Olson, Dairy Field, May, 1981, pp. 92 and 94; see also Quality Sweetness Control and Marketing Strategy Highlight the ACDPI Clinic, Rita McNiece, Dairy Field, May 1981, pp. 86 et seq at pg. 87.) External neutralization is discussed in a paper entitled Lactic Bulk Culture System Utilizing a Whey-based Bacteriopage Inhibitory Medium and pH Control, G. H. Richardson et al., Journal of Dairy Science, Vol. 60, No. 3, pp. 378-386, which describe the injection of gaseous ammonia or liquid ammonium hydroxide to control pH.

Internally buffered bulk starter media have also been formulated. A presently available commercial internally buffered starter medium contains pretested sweet dairy whey, phosphate-citrate buffers and autolyzed yeast (from label declaration of ingredients). An analysis of the product shows the major constituents to be magnesium, phosphorus and sodium. The exact composition of this internally buffered starter medium is not known. However, this starter medium suffers from various defects. The constituents of this starter tend to settle out and form insoluble lumps in the bottom of the starter vat if agitation is not maintained throughout starter propagation. The citrates encourage gas production during starter propagation which can result in the creation of undesirable foam during starter propagation.

Previous media have generally been formulated with an excessive amount of fermentable carbohydrates. This excess carbohydrate allows the bacteria to produce sufficient acid to overcome any buffer capacity present in the medium and thus the pH drops to a level determental to bacterial growth and viability.

In addition, most other starter media must be used within 16-20 hours from the time of inoculation, or refrigerated to extend their usable life.

It has now been found that these problems can be overcome by the present invention.

BRIEF SUMMARY OF THE PRESENT INVENTION

In accordance with the present invention, it has been found that a starter medium with internal pH control can be prepared by adding to the ingredients normal to a starter media an amount of magnesium monoammonium phosphate hexahydrate, also known in its mineral form as struvite, or the ingredients necessary for the preparation thereof in the starter medium. In theory, which applicant does not wish to be bound by, magnesium ammonium phosphate hexahydrate, is least soluble under alkaline conditions. As the fermentation proceeds acid is formed which allows for the solubilization of the magnesium ammonium phosphate hexahydrate. Triphosphate ions are then available to tie up hydrogen ions and control pH.

The present invention provides for the following: release of ammonium ions which are prime nutrients for the fermentation; pH control for higher cell population, enhanced cell viability permitting lower use of inoculum, shortening culturing times, and longer usable life without refrigeration; no external equipment required for pH control; better curd identity in the cheese making process; faster ripening for ripened cheeses; medium allowing for the use of limited carbohydrate; elimination of the need for continuous agitation during starter incubation and freedom from gas formation.

As used hereinafter the term magnesium ammonium phosphate is intended to refer to the hexahydrate salt though the disclosure is equally applicable to any magnesium ammonium salt which has lower solubility under mild alkaline conditions than under mild acid conditions (above pH 5).

DETAILED DESCRIPTION OF THE INVENTION

Magnesium ammonium phosphate is generally prepared as the hexahydrate by the following reaction

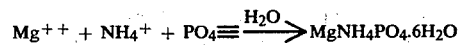

A specific reaction can be written as follows:

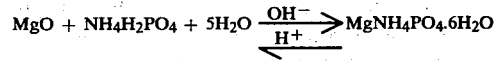

Magnesium ammonium phosphate hexahydrate is the main constituent of the mineral struvite. The magnesium ammonium phosphate as used in the invention can be prepared prior to addition to the medium or in situ in the medium. A magnesium salt can be mixed with a source of ammonia, (liquid or gaseous) or an ammonium salt plus a source of phosphate ions such as monoammonium or diammonium phosphate. Since the latter compounds provide both ammonium ions as well as phosphate ions, they are preferred as no extra ions need be added to the system. The reactants can be added in any order. However, the perferred order of addition is a magnesium salt, followed by a ammonium source to insure complete formation of the magnesium ammonium phosphate. The magnesium salts which can be used are any such salts which will react with the system including the oxide, hydroxide, carbonate, sulfate, chloride and the like. The phosphate ion can be derived from a salt or an acid such as phosphoric acid. If the magnesium ammonium phosphate is made externally of the bulk starter medium, any magnesium salt can be used since the conditions of reaction can be controlled. In preparing the magnesium ammonium phosphate in situ in the bulk starter medium, it is preferred to use magnesium oxide and magnesium hydroxide, preferably magnesium oxide and monoammonium phosphate. These ingredients can be added dry to the other ingredients of the medium, reaction taking place when they are dissolved. As a variant of the preceding, the ingredients can be dissolved in water and the entire bulk starter base dried as by spray or drum drying. At present, it apparently makes little difference whether the magnesium ammonium phosphate is formed externally or in situ so long as the proper amount is present in the medium.

It is essential that the starter medium have an initial pH within the range of from about 6.0 to about 7.5 and preferably about 6.5 to about 7.5 prior to fermentation. A more acidic pH results in less insoluble magnesium ammonium phosphate, such that it will not be available for neutralization of the acids produced during fermentation. An alkaline pH, particularly a pH above 8, inhibits microorganism growth.

The bulk starter medium also includes other ingredients normally present for bacterial growth including a carbohydrate source, other nitrogen containing growth stimulants and a source of vitamins and trace minerals, phage control agents and other pH control agents.

The basic ingredient of a bulk starter medium is a carbohydrate source, preferably a dairy derived product comprising protein and lactose. These products include whole milk, though this is less preferred, skim milk (liquid or dry) and whey (liquid or dry). Also included in the term dairy products are any products which are derived from milk or whey such as decalcified milk, partially clarified whey, delactosed whey, deproteinized/delactosed whey and the like. The latter have undergone some form of processing to remove certain desirable or undesirable compositions. The preferred milk bases are non-fat dried milk hereinafter "NFDM" and whey. The most preferred base is whey, particularly dried whey. Blends of milk and whey can also be used if desired. It is particularly preferred to use whey since it is economical and it does not contain casein which may coagulate during fermentation thereby requiring an agitation step to break-up the coagulum. The whey can be either sweet or acid whey though sweet whey is preferred.

The carbohydrate source can also be sugars or sugar containing products. The sugars are exemplified by lactose, sucrose, dextrose, fructose, and the like. Sugar containing products include, in addition to the dairy products described hereinbefore, corn syrup (particularly those with a high DE) hydrolyzed cereal solids and the like. It is also intended that the term carbohydrate source include blends of the aforementioned carbohydrate materials.

While the dairy derived product is a preferred source of carbohydrate, it is also preferable to incorporate sugars such as dextrose into the bulk starter base. Dextrose or other similar compounds such as fructose, maltose, and the like accelerate the initial development of the culture by reducing the initial lag phase of the culture. Any carbohydrates which are readily fermented by the lactic acid producing culture can be used. The term "sugar" is also intended to encompass lactose (containing less than 2.0% protein) which is added apart from the dairy derived product. Any decrease in the dairy derived product can be compensated by an increase in the carbohydrate content.

It is also important to incorporate in the bulk starter medium a nitrogen containing composition which acts as a stimulant for the growth of lactic acid producing bacteria. It has been found that polypeptide containing nitrogen sources such as hydrolyzed protein are effective in stimulating growth. Illustrative of compositions useful in this area are yeast extract, yeast autoylsate, yeast hydrolysate, solubilized yeast, yeast food, pancreas extract, amino acids, hydrolyzed plant and animal protein, hydrolyzed casein and mixtures thereof. Any nitrogen-containing or protein-containing source which will act as a growth stimulant can be used for this function. Non-protein nitrogen sources such as mono or diammonium phosphate also act as stimulants. It is particularly preferred to use both a non-protein nitrogen source and a hydrolyzed protein.

Trace vitamins and minerals of less than 1% and preferably less than 0.5% by weight of the bulk starter base can also be included for their known beneficial effects to lactic culture systems. These include B vitamins, ferrous sulfate, magnesium sulfate, and manganese sulfate. Generally, the Fe, Mg and Mn ions are present in the dairy derived ingredients or the autolyzed yeast.

The bulk starter medium can also include any ingredients normally used in bulk starter media which do not adversely affect the growth of the bacteria. Numerous useful ingredients are listed in Table I. The bulk starter medium can also contain phage control agents as are compatible with the media of the invention. These agents preferably include phosphate salts presently used for phage control such as mono and di alkali metal (Na and K) and/or ammonium orthophosphates, trisodium phosphate (TSP), pyrophosphates such as sodium acid or tetrasodium pyrophosphates, tripolyphosphates (Na and K), polyphosphates such as sodium hexametaphosphate and blends thereof. Citrates can also be used but are less desirable due to the tendency of media containing them to exhibit gas formation and reduced curd strength. The preferred phage control agents are the alkali metal tripolyphosphates, the sodium salt being most preferred. Sodium tripolyphosphate (STPP) generally is composed of about 85% sodium tripolyphosphate, 7–10% sodium pyrophosphate and 3–5% sodium metaphosphate. It is preferred that the STPP evidence little change in pH on heating.

Blends of phosphate and citrates can also be effective in phage control.

The bulk starter base is generally comprised of from about 15 parts to about 60 parts and preferably from about 30 parts to about 40 parts carbohydrate. Since the preferred sweet whey has approximately 70% carbohydrate, sweet whey is preferably used in an amount ranging from about 20 parts to about 85 parts. Also included in the term carbohydrate is any sucrose or dextrose added as a growth accelerator. The amount of carbohydrate source which can be used can be easily computed from the carbohydrate content thereof. The bulk starter base also includes compositions sufficient to provide from about 1 part to about 7.5 parts and preferably from about 2.0 parts to about 4.0 parts ammonium ion. These levels of ammonium ion can be obtained through the use of monoammonium phosphate, diammonium phosphate, or combinations thereof, and preferably from monoammonium phosphate. The base also contains compositions sufficient to provide from about 1 part to about 10 parts and preferably from about 3.0 parts to about 6.0 parts of magnesium ion. The base also includes compositions sufficient to provide from about 4 parts to about 40 parts and preferably from about 10 parts to about 25 parts phosphate ions. The magnesium ion and the ammonium ion are present in an amount sufficient to react with the phosphate ion to provide an amount of magnesium ammonium phosphate sufficient to maintain the pH of the fermentation above 5 for at least 20 hours. The bulk starter base can also optionally contain a phage control agent, preferably a phosphate phage controlling agent, in an amount ranging from about 1 part to about 25 parts. This phosphate is in addition to above forementioned phosphate. These amounts are also governed by the functional characteristics of fermentation. The degree of fermentation desired is controlled by the amount of carbohydrate present. Since the amount of carbohydrate determines the extent of fermentation it also determines the amount of acid produced. The greater the amount of carbohydrate the greater the amount of acid produced, and hence the greater the amount of buffering (magnesium-ammonia phosphate reaction product) needed to maintain the pH of the medium above 5. Bacterial growth greatly diminishes below pH 5.

Since the bacteria do not propagate above a pH of 8, the initial starter medium as prepared from the base must have a pH below 8.0 and preferably below 7.5. If an acid such as citric acid is added as a phage control agent, neutralizing agents (alkaline phosphates) must if necessary, be added to elevate the pH within the proper range. If the phage control agent is an alkaline phosphate, an acidic compound must be added to reduce the pH within the proper range. Monoammonium phosphate is particularly desirable for this use since it provides necessary ions for the formation of insoluble magnesium ammonium phosphate as well as acidity. A sufficient excess is therefore used to provide a liquid medium with a final pH within the range of from about 6 to about 7.5 and preferably from about 6.5 to about 7.5. The nitrogen-containing growth nutrient, other than ammonium ion added as the magnesium ammonium phosphate or the mono and/or diammonium phosphates, can be used in any amount up to 20 parts and preferably from about 2 parts to about 10 parts, but above 20 parts appears to have little beneficial effect. The amounts of other ingredients normally used in bulk starter media can be easily calculated from the aforegoing numbers. The parts given hereinbefore are by weight per 100 parts of bulk starter base comprised of the weight of the carbohydrate sources, the combined ammonium ion source, phosphate ion source and the magnesium ion source, the nitrogen containing nutrient and, if present, the phage control agent, trace minerals and vitamins.

Any bulk starter medium and particularly any dairy product used in preparing the bulk starter medium is preferably pasteurized prior to inoculation to destroy any microorganism which might interfere with the preparation of the bulk starter for the cheese making process. The pasteurization can be high heat/short time or low heat/long time though the latter is preferred. It is noted that any starter prepared with milk can curd because of the presence of casein. A curded starter can be agitated prior to use to breakup the curds.

The purity of the dairy derived products and especially the whey is of importance to the cheese manufacturer. Since the bulk starter medium becomes part of the final cheese product, care is taken to avoid using any component in the starter medium which will have any adverse effect on the cheese. Traditionally, starter media have not been made from whey containing coloring matter such as annatto which is used in the manufacture of yellow cheddar cheese and other colored varieties. Whey from mozzarella or other non-colored varieties is preferred because of its lack of of coloring. It is also important that the initial level of microorganisms in the whey is low. The pasteurization conditions normally used in preparing the starter medium will kill a large proportion of the bacteria but are not effective to sterilize the medium. As such, the lower the number of bacteria in the initial whey, the lower will be the amount of bacteria remaining after pasteurization.

In general, a starter base is formulated from ingredients which appear in the final product to reduce the shock effect on the bacteria. For dairy use such as cheese manufacturing dairy derived products, such as whey, form an excellent base for the starter medium.

While the liquid bulk starter medium can be blended for the cheese manufacturer, it is usually prepared by the manufacturer himself. A dry solids blend of the ingredients in the medium is provided to the cheese manufacturer, known as a bulk starter base. The cheese manufacturer can dissolve the base to the correct percent solids in an aqueous solution to form the starter medium.

A bulk starter medium can be prepared by blending the bulk starter base with water in an amount sufficient to provide from about 6% to about 12% by weight solids of the medium, the balance being water. The blending of the bulk starter base and the water are accomplished using normal procedures of reconstitution as presently used in the industry in preparing bulk starter media. These procedures include pasteurization of the bulk starter medium, preferably using low temperature/long time conditions.

Also included within the scope of the invention is the preparation of a bulk starter base preblend. The preblend would include all the nutrients normally included in the base without all or a part of the carbohydrate source such as the dairy derived product. The preblend can be used in combination with a dry dairy derived product such as NFDM or dry whey and water to prepare the starter medium. The water can be added as part of a liquid dairy derived product such as whey. The percentage of ingredients are those needed to form the starter base as stated hereinbefore. The use of the preblend is less preferred since the manufacturer of the base has no control over the quality of the dairy derived ingredients which are used in preparing the final starter medium. For the reasons outlined hereinbefore, the type of whey, its origin, purity and the absence of coloring matter are extremely important to the cheese manufacturer who uses the bulk starter medium.

The bulk starter base or the preblend can be prepared by dry blending, under good manufacturing techniques for foods, the ingredients thereof. The bulk starter base or preblend can also be prepared by wet blending the ingredients and co-drying the blend. The entire wet blend can be pasteurized prior to drying if desired. The water portion can be obtained from water of liquid ingredients such as liquid milk or whey. It is also included within the invention that the magnesium ammonium phosphate can be prepared and the liquid reaction mixture be combined with the other ingredients and dried. Drying can be accomplished using any type of drying system which will not adversely affect the product such as spray drying and drum drying, with spray drying being preferred.

A preferred bulk starter base comprises: from about 36% to about 54% sweet whey; from about 5% to about 7% autolyzed yeast; from about 6% to about 9% magnesium oxide; from about 24% to about 36% monoammonium phosphate; and from about 10% to about 14% sodium tripolyphosphate. The pH of the above bulk starter base when reconstituted in water is between 6.5 and 7.5 prior to fermentation. These percentages are based on the combined weight of the above items, the total equalling 100%.

The bulk starter medium of the present invention can be used to culture various bacterial cultures, preferably those used to make bulk starter which include: S. lactis, S. citrovorous, S. cremoris, S. paracitrovorous, S. durans, S. thermophilus, S. faecalis, S. diacetylactis, L. helveticus, L. acidophilus, L. bulgaricus, L. citrovorum, L. brevis, L. delbrueckii, L. lactis, L. fermenti, L. mesenteroides, L. plantarum, Propionibacterium species and mixtures thereof. It is desirable to vary the culture on successive batches of cheese or use mixtures of cultures. It is therefore important that a wide variety of bacteria be tolerant to the bacteriophage control system.

Bacteria can be added to the starter medium, which is preferably pasteurized, in any amount sufficient to provide the starter. The bacteria is usually added to the medium in amounts recommended by the culture suppliers. The bacteria are cultured for the necessary growout time which is typical of the bacteria. These times generally range from about 12 to 24 hours.

The starters prepared thereby can be used immediately or held at room temperature up to 72 hours. Temperatures between freezing and about 10° C. are preferred for cooled storage.

The starter can be used to inoculate pasteurized milk as per the common practice of the cheese industry. The starter is generally used in amounts large enough to provide desired bacteria levels and generally in amounts ranging from about 1% to about 6% and preferably about 3% to 5.0%.

The present invention is more specifically illustrated in the examples which follow. The term commercial starter culture used in the following examples indicates that a commercial starter culture was used but not necessarily the same in all examples.

EXAMPLE 1

The following ingredients were dry blended:

TABLE

| Ingredients | Weight Grams | % Dry Basis |
|---|---|---|
| Magnesium Oxide (MgO) | 5 | 8 |
| Monoammonium Phosphate (MAP) | 18 | 28 |
| Sodium Tripolyphosphate (STPP) | 7 | 11 |
| Autolyzed Yeast (Amberex 1003) | 4 | 6 |
| Sweet Whey(dry) | 31 | 48 |

The dry blend was mixed with 900 grams water and the so prepared medium was heated to 85° C. for 45 minutes to pasteurize it. After cooling, the medium was inoculated with 0.005% by weight based on the weight of the medium of a thawed commercial frozen starter culture concentrate. The starter was incubated at room temperature. The following data was obtained during incubation, indicating a useable starter culture was maintained for 64 hours:

TABLE

| Time | pH | Gel Time* |
|---|---|---|
| 0 | 7.23 | — |
| 64 hours | 4.96 | 4 hours, 16 minutes |

*Time required for a 10% solution of reconstituted non-fat dry milk pasteurized at 72° C. for 16 seconds and cooled to 37° C. and inoculated with 3% of starter to coagulate.

EXAMPLE 2

The following ingredients were dry blended in a commercial scale ribbon blender:

TABLE

| Ingredients | Weight | Percentage By Weight |
|---|---|---|
| Sweet Whey(dry) | 828 kg. | 45.32 |
| Autolyzed Yeast Extract (Amberex 1003) | 54 kg. | 2.96 |
| Autolyzed Yeast Extract (Amberex 100) | 54 kg. | 2.96 |
| Magnesium Oxide | 135 kg. | 7.39 |
| Monoammonium Phosphate | 540 kg. | 29.56 |
| Sodium Tripolyphosphate | 216 kg. | 11.82 |
| | | 100.01 |

The product was packaged in 27 kg. (60 lb.) bags. A random sample was taken from 1 bag and 35 grams of the sample was added to 465 grams of water under agitation. The so prepared medium was then pasteurized and inoculated as in Example 1. The following data were obtained after incubation at room temperature, indicating a useable starter life of at least 28 hours:

TABLE

| Incubation Time | pH | Gel Time |
|---|---|---|
| 0 | 7.22 | — |
| 15.5 hours | 5.90 | 5 hours, 11 minutes |
| 19.5 hours | 5.44 | 4 hours, 12 minutes |
| 23.5 hours | 5.18 | 4 hours, 9 minutes |
| 28 hours | 5.01 | 5 hours, 20 minutes |

EXAMPLES 3–9

The following media were prepared in the laboratory using the procedure of Example 1. All amounts are in grams:

| No. | 3 | 4 | 5 | 6 | 7 | 8 | 9 |
|---|---|---|---|---|---|---|---|
| Water | 900 | 900 | 900 | 900 | 900 | 900 | 900 |
| Aut. Yeast (Amberex 1003) | 2 | 2 | 2 | 2 | 2 | 2 | 2 |
| Aut. Yeast (Amberex 100) | 2 | 2 | 2 | 2 | 2 | 2 | 2 |
| Whey Solids | 30 | 30 | 30 | 30 | 30 | 30 | 30 |
| STPP | 8 | 8 | 8 | 8 | 8 | 8 | 8 |
| MAP | 20 | 20 | 20 | 17 | 24 | 20 | 15 |
| MgO | 5 | 4 | 6.5 | 5 | 5 | 7 | 5 |

The above media were pasteurized and inoculated as in Example 1. The inoculated media were incubated at room temperature and the following data obtained:

TABLE

| | | Approximate Incubation Time | | | | | |
|---|---|---|---|---|---|---|---|
| | 0 Hours | 17 Hours | | 24 Hours | | 41 Hours | |
| No. | pH | pH | Gel Time | pH | Gel Time | pH | Gel Time |
| 3 | 6.97 | 5.67 | 4'13" | 5.48 | 4'08" | 5.12 | 4'20" |
| 4 | 6.78 | 5.53 | 4'12" | 5.15 | 4'07" | 4.81 | 4'21" |

TABLE-continued

| No. | 0 Hours pH | Approximate Incubation Time | | | | | |
|---|---|---|---|---|---|---|---|
| | | 17 Hours | | 24 Hours | | 41 Hours | |
| | | pH | Gel Time | pH | Gel Time | pH | Gel Time |
| 5 | 7.42 | 5.84 | 4'21" | 5.61 | 4'10" | 5.46 | 4'16" |
| 6 | 7.23 | 5.79 | 4'21" | 5.52 | 4'07" | 5.12 | 4'14" |
| 7 | 6.70 | 5.57 | 4'16" | 5.37 | 4'07" | 5.06 | 4'23" |
| 8 | 8.02 | 7.88 | DNG | 7.84 | DNG | 7.56 | DNG |
| 9 | 8.12 | 7.90 | DNG | 7.86 | DNG | 7.15 | DNG |

DNG—Did not gel.

The above data indicates that media 3–7 were acceptable for propagation of starter culture, while media 8 and 9 were not.

EXAMPLE 10

Various salts were tried in a medium using 60 grams dry whey, 20 grams NFDM, 4 grams yeast autolysate, 3–11 grams monoammonium phosphate and 5 grams of diammonium phosphate to a total of about 100 grams. The buffering salts were added at a 6.5 gram level. The procedure of example 1 was used. The following salts were tried:

Monocalcium Phosphate
Dicalcium Phosphate
Calcium Carbonate
Magnesium Carbonate
Tricalcium Phosphate
Magnesium Oxide
Magnesium Hydroxide The only salts which effectively buffered the medium under these conditions were magnesium oxide and magnesium hydroxide.

What is claimed is:

1. A bulk starter base comprising:
   (a) a carbohydrate source:
   (b) an effective amount of a nitrogen containing growth stimulant;
   (c) an alkali metal tripolyphosphate phage control agent;
   (d) and sufficient ammonium ion, phosphate ion, and magnesium ion to provide magnesium ammonium phosphate sufficient to maintain the pH of the cultured bulk starter medium above at least pH 5 for at least 20 hours;
   the initial pH prior to fermentation being from 6 to about 7.5, said magnesium ammonium phosphate being less than 50% soluble at said initial pH.

2. The bulk starter base as recited in claim 1 wherein said carbohydrate source is a lactose-containing dairy derived product.

3. The bulk starter base as recited in claim 2 wherein said dairy derived product is whey.

4. The bulk starter base as recited in claim 2 wherein said growth stimulant is selected from the group consisting of hydrolyzed plant protein, hydrolyzed animal protein, hydrolyzed yeast and autolyzed yeast.

5. The bulk starter base as recited in claim 4 wherein said growth stimulant is autolyzed yeast.

6. The bulk starter base as recited in claim 1 wherein said carbohydrate source is present in an amount ranging from about 15 parts to about 60 parts based on 100 parts of said bulk starter base.

7. The bulk starter base as recited in claim 1 wherein said magnesium ion is present in an amount ranging from about 1 parts to about 10 parts per 100 parts of said bulk starter base.

8. The bulk starter base as recited in claim 1 wherein said phosphate ion is present in an amount ranging from about 4 parts to about 40 parts per 100 parts of said bulk starter base.

9. The bulk starter base as recited in claim 1 wherein said alkali metal tripolyphosphate is sodium tripolyphosphate.

10. The bulk starter base as recited in claim 1 wherein said alkali metal tripolyphosphate is present in an amount ranging from about 1 parts to about 25 parts per 100 parts of bulk starter base.

11. A bulk starter base comprising:
    (a) from about 20 parts to about 85 parts of a lactose-containing dairy derived product;
    (b) from about 1 parts to about 20 parts of a nitrogen-containing growth stimulant;
    (c) an alkali metal tripolyphosphate phage control agent; and
    (d) sufficient magnesium, ammonium, and phosphate ions to provide from about 10 parts to about 55 parts of magnesium ammonium phosphate, the pH of said base in water being from about 6 to about 7.5 prior to fermentation.

12. The bulk starter base as recited in claim 11 wherein said dairy derived product is whey.

13. The bulk starter base as recited in claim 11 wherein said growth stimulant is autolyzed yeast.

14. The bulk starter base as recited in claim 11 wherein the initial pH when reconstituted in water ranges from about 6.5 to about 7.5.

15. The starter base as recited in claim 11 wherein said magnesium ammonium phosphate has been formed from a blend of magnesium oxide, magnesium hydroxide or mixtures thereof said monoammonium phosphate in molar ratio of about 1:1 in an amount sufficient to neutralize the acid formed during fermentation to maintain the pH of the bulk starter medium above at least about pH 5 for at least about 20 hours, the initial pH of said base in water being from about 6 to about 7.5 prior to fermentation.

16. The bulk starter base as recited in claim 15 wherein said dairy derived product is whey.

17. The bulk starter base as recited in claim 15 wherein said growth stimulant is autolyzed yeast.

18. The bulk starter base as recited in claim 15 wherein said magnesium compound is magnesium oxide.

19. The bulk starter base as recited in claim 11 wherein said alkali metal tripolyphosphate is sodium tripolyphosphate.

20. The bulk starter base as recited in claim 15 wherein said base comprises:
    (a) from about 36% to about 54% sweet whey;
    (b) from about 5% to about 7% autolyzed yeast;
    (c) from about 6% to about 9% magnesium oxide;
    (d) from about 24% to about 36% monoammonium phosphate; and
    (e) from about 10% to about 14% sodium tripolyphosphate;
the pH of said base in water being between 6.5 and 7.5 prior to fermentation, said percentages being based on the combined dry weight of items (a), (b), (c), (d), and (e).

21. The bulk starter base as recited in claim 20 wherein said base is dry.

22. The bulk starter base as recited in claim 20 wherein said base is a dry product prepared by dry blending items (a)–(e) in dry form.

23. A method for preparing a starter comprising culturing a starter culture in a starter base comprising:
(a) a carbohydrate source;
(b) an effective amount of a nitrogen containing growth stimulant;
(c) an alkali metal tripolyphosphate phage control agent; and
(d) ammonium phosphate and magnesium ions sufficient to provide an amount of magnesium ammonium phosphate effective to neutralize at least 10% of the acid formed by fermentation, the pH of the bulk starter base in water being from about 6 to about 7.5 prior to fermentation and said magnesium ammonium phosphate being less than 50% soluble at said pH.

24. The method for preparing a starter as recited in claim 23 wherein said starter base comprises:
(a) from about 36% to about 54% sweet whey;
(b) from about 5% to about 7% autolyzed yeast;
(c) from about 6% to about 9% magnesium oxide;
(d) from about 24% to about 36% monoammonium phosphate; and
(e) from about 10% to about 14% sodium tripolyphosphate;
the pH of said base in water being between 6.5 and 7.5 prior to fermentation, said percentages being based on the combined dry weight of items (a), (b), (c), (d), and (e).

25. A bulk starter base comprising:
(a) from about 36% to about 54% of a lactose-containing dairy derived product;
(b) from about 5% to about 7% of a nitrogen-containing growth stimulant;
(c) from about 6% to about 9% of a magnesium compound selected from the group of magnesium oxide, magnesium hydroxide and mixtures thereof:
(d) from about 24% to about 36% monoammonium phosphate; and
(e) from about 10% to about 14% of an alkali metal tripolyphosphate;
the pH of said base in water being from about 6.0 to about 7.5 prior to fermentation, said percentages being based on the combined dry weight of items (a), (b), (c), (d), and (e).

26. The bulk starter base as recited in claim 25 wherein said dairy derived product is whey.

27. The bulk starter base as recited in claim 25 wherein said growth stimulant is selected from the group consisting of hydrolyzed plant protein, hydrolyzed animal protein, hydrolyzed yeast and autolyzed yeast.

28. The bulk starter base as recited in claim 27 wherein said growth stimulant is autolyzed yeast.

29. The bulk starter base as recited in claim 25 wherein said alkali metal tripolyphosphate is sodium tripolyphosphate.

30. The bulk starter base as recited in claim 25 wherein said magnesium compound is magnesium oxide.

31. A bulk starter base comprising:
(a) from about 36% to about 54% sweet whey;
(b) from about 5% to about 7% autolyzed yeast;
(c) from about 6% to about 9% magnesium oxide;
(d) from about 24% to about 36% monoammonium phosphate; and
(e) from about 10% to about 14% sodium tripolyphosphate;
the pH of said base in water being from about 6.0 to about 7.5 prior to fermentation, said percentages being based on the combined dry weight of items (a), (b), (c), (d), and (e).

32. The bulk starter base as recited in claim 31 wherein said base is dry.

33. The bulk starter base as recited in claim 31 wherein said base is a dry product prepared by dry blending items (a)–(e) in dry form.

* * * * *

UNITED STATES PATENT AND TRADEMARK OFFICE
CERTIFICATE OF CORRECTION

PATENT NO. : 4,402,986
DATED : September 6, 1983
INVENTOR(S) : B. A. Sinkoff - R. H. Bundus It is certified that error appears in the above-identified patent and that said Letters Patent are hereby corrected as shown below:

Claim 15, line 4 (at Col. 12, line 34) delete "said" and insert -- and --.

Signed and Sealed this

Twenty-seventh Day of March 1984

[SEAL]

Attest:

GERALD J. MOSSINGHOFF

Attesting Officer     Commissioner of Patents and Trademarks